United States Patent
Luan et al.

(10) Patent No.: US 10,850,122 B2
(45) Date of Patent: Dec. 1, 2020

(54) OPTIMIZATION METHODS FOR RADIATION THERAPY PLANNING

(71) Applicant: STC.UNM, Albuquerque, NM (US)

(72) Inventors: Shuang Luan, Albuquerque, NM (US); Daniel Andres Riofrio Almeida, Quito (EC)

(73) Assignee: STC.UNM, Albuquerque, NM (US)

( * ) Notice: Subject to any disclaimer, the term of this patent is extended or adjusted under 35 U.S.C. 154(b) by 240 days.

(21) Appl. No.: 15/843,706

(22) Filed: Dec. 15, 2017

(65) Prior Publication Data

US 2018/0111006 A1   Apr. 26, 2018

Related U.S. Application Data

(63) Continuation of application No. 15/304,306, filed as application No. PCT/US2015/028558 on Apr. 30, 2015, now Pat. No. 9,844,684.

(60) Provisional application No. 61/986,526, filed on Apr. 30, 2014, provisional application No. 62/048,709, filed on Sep. 10, 2014.

(51) Int. Cl.
| | |
|---|---|
| *A61N 5/10* | (2006.01) |
| *G06N 3/00* | (2006.01) |
| *G06F 19/00* | (2018.01) |
| *G16H 20/40* | (2018.01) |

(52) U.S. Cl.
CPC ............. *A61N 5/1031* (2013.01); *A61N 5/10* (2013.01); *A61N 5/1001* (2013.01); *A61N 5/103* (2013.01); *A61N 5/1007* (2013.01); *G06F 19/325* (2013.01); *G06N 3/006* (2013.01); *G16H 20/40* (2018.01); *A61N 5/1084* (2013.01); *A61N 2005/101* (2013.01); *A61N 2005/1024* (2013.01); *A61N 2005/1034* (2013.01)

(58) Field of Classification Search
CPC ...... A61N 5/10; A61N 5/1001; A61N 5/1007; A61N 5/1031; A61N 2005/1034; A61N 5/1084; A61N 2005/1024
USPC .......................................................... 378/65
See application file for complete search history.

(56) References Cited

U.S. PATENT DOCUMENTS

| | | | |
|---|---|---|---|
| 7,899,517 B2 * | 3/2011 | Kindlein .............. | A61N 5/1031 600/1 |
| 9,262,583 B2 * | 2/2016 | Madabhushi .......... | G06T 7/143 |
| 9,492,683 B2 * | 11/2016 | Brachman ............ | A61N 5/1007 |
| 9,844,684 B2 * | 12/2017 | Luan .................... | A61N 5/1031 |
| 10,515,412 B2 * | 12/2019 | Rocklitz ................ | G06Q 40/06 |

* cited by examiner

*Primary Examiner* — Allen C. Ho
(74) *Attorney, Agent, or Firm* — Valauskas Corder LLC

(57) ABSTRACT

An optimization technique for use with radiation therapy planning that combines stochastic optimization techniques such as Particle Swarm Optimization (PSO) with deterministic techniques to solve for optimal and reliable locations for delivery of radiation doses to a targeted tumor while minimizing the radiation dose experienced by the surrounding critical structures such as normal tissues and organs.

20 Claims, 5 Drawing Sheets

Data: Kinetic particle swarm, $K$; static particle pre-computed potential, $U_S$.

Result: $K_t$.

Set $t \leftarrow 0$;

Set $K_{t-1} \equiv Inf$ and $K_t \equiv K$;

while $t < T_{max}$ and $metric(K_{t-1}, K_t) \geq \xi$ do

For each $p_i \in K_t$ calculate $\sum_i \vec{F}_i$ using equation 1.2;

Update $K_{t-1} \leftarrow K_t$;

Update $K_t$ using the motion equations 1.4 and 1.5;

Set $t \leftarrow t + 1$;

end

Return $K_t$;

OPTIMIZATION METHODS FOR RADIATION THERAPY PLANNING

CROSS-REFERENCE TO RELATED APPLICATIONS

This application is a continuation of U.S. patent application Ser. No. 15/304,306, now U.S. Pat. No. 9,844,684, which is a National Stage Entry of International Application No. PCT/US15/28558 filed Apr. 30, 2015, which claims the benefit of U.S. Provisional Patent Application No. 61/986,526 filed Apr. 30, 2014, and U.S. Provisional Patent Application No. 62/048,709 filed Sep. 10, 2014, both incorporated by reference.

STATEMENT REGARDING FEDERALLY SPONSORED RESEARCH OR DEVELOPMENT

This invention was made with government support under CBET 0853157 awarded by the National Science Foundation (NSF). The government has certain rights in the invention.

FIELD OF THE INVENTION

The invention relates generally to radiation therapy. More specifically, the invention is directed to an optimization technique that combines stochastic optimization techniques with deterministic techniques to solve for optimal locations of radiation sources for use with radiation therapy planning.

BACKGROUND OF THE INVENTION

Cancer is a wide spread disease that expresses itself through the errant growth of abnormal cells. If the uncontrolled growth of these cells is not stopped, it can be fatal. The fatal trend of cancer worldwide is steadily increasing along with the overall estimated cost for cancer management. This has led to an increased demand from the general public to develop more effective tools and technologies for treating and curing the disease. With the rapid advancement of medical imaging, tumors are being diagnosed in early stages when they are still local or regional. Radiation therapy, brachytherapy, particle therapy, and chemotherapy are effective in treating local cancel cells, or tumors.

Radiation therapy uses ionizing radiation to control or kill malignant cells. Brachytherapy uses radioactive sources to treat malignant cells at short-range. Particle therapy uses beams of energetic protons, neutrons, or positive ions for cancer treatment. Chemotherapy is the invasive use of drugs to target and kill malignant cells.

Radiation therapy is a modality of cancer treatment that uses ionizing radiation (e.g., high energy X-rays) that damages the DNA and causes cell death within the region being irradiated. Hence, the goal of radiation therapy is to deliver a radiation dose high enough to kill all the targeted tumor cells while simultaneously minimizing the damage to surrounding normal structures. The quality of a radiotherapy plan is usually judged by its dose conformity and treatment time. The dose conformity describes how well the high radiation dose region conforms to the targeted tumor and spares the surrounding normal tissues, while treatment time describes how long treatment takes and the efficiency of the treatment machines used. Any improvement in the dose conformity in radiation therapy likely improves tumor control and reduces the likelihood of complications, and any improvement in treatment time likely lowers the treatment cost and improves patient throughput and comfort.

Many types of ionizing radiation have been experimented through the history of radiotherapy. These include high energy photons (e.g., y-rays and high energy X-rays), electrons, and charged particles heavier than electrons such as protons, pions, alpha particles, carbon ions, and even anti-protons.

In order to provide dose conformity and efficient treatment time, radiotherapy relies on specialized optimization algorithms, for instance simulated annealing, deterministic optimization models such as linear programming, non-negative least squares, linear programming, among others; genetic algorithms, neural networks, mixed integer linear programming, and graph algorithms, etc. Usually these algorithms try to model all competing treatment goals and radiation source configurations as a unique optimization problem.

Modern radiation therapy treatment planning typically involves the following set of steps: patient imaging, target definition (i.e., structure contouring), dose prescription, beam configuration optimization, plan generation, and quality assurance.

Imaging is performed by taking computer tomography scans (CT scans), magnetic resonance imaging (MRI), positron emission tomography (PET), ultrasound or combinations of these depending on the type of cancer. CT scan is the most widely used imaging modality and can provide anatomical information of the patient. Once these images are obtained, physicians contour the tumor and organs at risk (OARs) as well as prescribe the desired dose to treat the tumor.

Modern radiation therapy relies on computer based optimization algorithms and software to generate the beam configuration for delivering the prescribed treatment.

Generally speaking, a treatment planning system includes the following functionalities in order to provide an optimal treatment:

(1) Patient Representation in which the computational model of a patient is represented as a three dimensional voxel array with resolution inherited from the type of imaging used (e.g., 1 mm×1 mm×1 mm). While contouring is performed, each voxel is associated with a particular structure which allows the identification of tumor voxels (target) versus organ-at-risk voxels.

(2) Ideal Dose Distribution is aided by the prescription obtained from the physicians and a desired dose distribution is generated. A desired dose distribution usually consists of a maximum and minimum dose tolerance per structure. There are many ways to represent this ideal dose distribution. As an example, the ideal dose distribution is assumed as a two three-dimensional array of dose values corresponding to a maximum and minimum tolerance per structure's voxel.

(3) Preparation for Dose Calculation includes the goal of treatment planning to select a subset of beam configurations (e.g., beam energies, locations, angles, size, etc.) from a set of candidate beam configurations that can meet the ideal or prescribed dose distribution. Beam configurations are usually selected using randomized sampling or by applying other optimization algorithms. Once beam configurations are selected, the dose contribution from each candidate beam configuration is calculated before beam-on time optimization. This fact imposes a constraint on the cardinality of the candidate beam configurations set, since it is a process bounded by the amount of memory RAM available in the system.

(4) The conceptual optimization problem in radiation therapy may be stated as:

$$\underset{t}{\text{minimize}} \left\| \sum \dot{D}_j t_j - D^* \right\| \text{ subject to } t_j \geq 0,$$

where $D^*$ is the ideal dose distribution or prescribed dose. $\dot{D}_j$ is the dose rate contributed by the j-th candidate beam, and $t_j$ is the weighting or beam-on time for the j-th beam. The constraint $t_j \geq 0$ reflects that the beam-on time must be non-negative. Thus the goal of the optimization is to find the beam-on times $t_j$ so that the created dose distribution $\Sigma_j \dot{D}_j \times t_j$ is as close to $D^*$ as possible. In certain situations, there may be an additional constraint such as that the total beam-on time must be below a certain threshold. The optimization problem may be viewed as a constrained least square problem.

(5) Plan Generation that processes the optimal result in order to generate a set of instructions compatible with the radiation modality and technology used. The plan is reviewed and tested as part of quality assurance.

Optimization is a fundamental tool in science, and it can be defined as the systematic process to achieve a pre-specified purpose. Generally speaking, the purpose is related to two states: maximize a benefit or minimize an effort. Optimization algorithms are classified according to different aspects of their formulation, for instance, according to the nature of their objective function, they can be linear, non-linear, quadratic, convex, concave, differentiable, non-differentiable, etc. According to the domain of the decision variables, they can be continuous or discrete. In addition, they can be classified according to the method of operation into two groups: deterministic and probabilistic algorithms.

Deterministic algorithms such as least-distance programming, non-negative least squares, least squares, etc. are used when there exists a clear understanding of the characteristics of the possible solutions and their utility for a given problem. When there is not a clear understanding of a possible solution and its utility or the search space has high dimensionality, these algorithms may not succeed in finding a solution. Then, probabilistic algorithms are used. Probabilistic or stochastic algorithms are those that sample the space of possible solutions for a given problem and through heuristics iteratively improve the solution.

The main goal of radiation therapy is to deliver a lethal dose of radiation to the targeted tumor while minimizing the radiation dose to the surrounding normal tissues and critical organs. Modern cancer therapy has benefited enormously from computer controlled treatment devices with increased precision and capability. However, this increased sophistication also creates new challenges for treatment planning. As the number of parameters in a treatment plan increases, the traditional computational approaches are no longer adequate to fully exploit the potential of the latest treatment devices. This is because at the heart of treatment planning is often a set of substantially non-trivial constrained geometric optimization problems.

Thus, there is a need for improved treatment planning using superior optimization techniques to solve for optimal and reliable locations for delivery of radiation doses to a targeted tumor while minimizing the radiation dose experienced by the surrounding critical structures such as normal tissues and organs. The invention satisfies this need.

SUMMARY OF THE INVENTION

The invention combines the flexibility of a stochastic optimization method, i.e., particle swarm optimization (PSO) with the maturity and fast convergence of deterministic optimization methods (e.g., non-negative least squares, least-distance programming, least squares optimization, etc.).

For PSO, the classical view of a particle representing a potential solution of the optimization function is extended by using the whole particle distribution as the solution. Tumors, critical organs and other tissues are modeled as geometric volumes, whose surfaces have an associated potential function. The radiation source is modeled as kinetic particles subject to the forces from the potential functions from both the particles and the various geometric objects. The final configuration of the swarm of particles including their trajectories is the treatment plan, e.g., radiation source location such as a beam location or interstitial implant trajectories. With the final configuration of the swarm, radiation may be delivered to a tumor mass with minimum or no damage to the critical structures (i.e., organs).

In contrast, the classical PSO algorithm consists of an iterative algorithm that uses the notion of individuals carrying potential solutions to the problem one is trying to solve. A set of individuals comprise the swarm, and each individual, i.e., a potential solution, in the swarm is represented by a multidimensional location vector and a velocity vector. With each iteration, the location and the velocity vectors are updated based on the current velocity and both the best location each individual has explored and the global best location the swarm has explored. This process repeats for a fixed number of iterations or until a desired minimum error is achieved or a desired fitness level is achieved by one individual. Finally, the individual that has visited the best location is the one carrying the optimal solution. However, as applied to radiation therapy planning, classical PSO modeling is not used where a particle or individual represents a potential solution of the optimization problem; instead, the whole swarm is the solution.

For purposes of this application, the invention focuses on two radiation therapy modalities: Gamma Knife® radiosurgery and High-Dose Rate Brachytherapy; however, any radiation therapy modality is contemplated including a particle therapy machine or a lower dose rate Brachytherapy seed.

Radiosurgery is a radiation therapy technique based on the principle that a single high dose of radiation delivered precisely to a small area will arrest or kill the tumor. Hence, radiosurgeries usually use a number of precisely aimed highly focused external beams of radiation to target a specific area. Gamma Knife® radiosurgery uses the y-ray radiations from cobalt-60 ($^{60}$Co) sources to eradicate tumors. The sources (typically about 200) are arranged either in a torus or hemisphere (depending on the machine model), and the rays emitted are focused at a single point (called the iso-center or focus), which creates a spherical high dose volume. A Gamma Knife® procedure is essentially a "ball-packing" process, where the goal is to pack the spherical high dose volumes into a target tumor volume and create a radiation dose deposition that conforms to the target tumor volume and spares the surrounding normal tissues and structures. Even though there are some attempts to develop automatic planning systems for Gamma Knife® the procedure is still planned by physicians manually using a "trial-and-error" approach.

In one embodiment according to the invention, the Gamma Knife® dose kernels (i.e., high density dose volumes generated by the superposition of radiation beams produced by the Gamma Knife® machine) are mapped to kinetic particles inside the tumor with zero initial velocity. After these particles stabilize, a non-negative least squares algorithm is used to filter-out redundant radiation sources and efficiently shape the final dose distribution. The prescribed dose is an input parameter provided by the physician.

Brachytherapy is a radiation therapy modality in which the tumor is eradicated by placing small radioactive isotope sources in short range of a tumor. In one embodiment, the optimization technique according to the invention is applied to the interstitial high-dose rate (HDR) brachytherapy treatment for prostate cancers, which is the most common disease among men in the United States and the second leading cause of death.

Generally speaking, HDR brachytherapy treatment involves the following key steps. First, the physician inserts the interstitial catheters or implants (i.e., hollow needles with bevel tips) inside the prostate under ultrasound guidance. After enough needles (typically about 20) are placed, they are hooked up to an after-loader unit. After contouring is performed, a computer program, typically based on linear programming or simulated annealing, is used to calculate the dwell-time of the source at each location along the needles. Then, the after-loader unit (containing an iridium-192 ($^{192}$Ir) source) then sends the radioactive source through the hollow needles one by one to deliver the radiation dose to the target.

Not surprisingly, the biggest challenge for HDR brachytherapy for prostate cancer is the needle placement. There are no computer algorithms to calculate the needle positions. As a result, the needles are placed in real time and the physician tends to use many more needles than necessary to ensure proper coverage of the entire prostate. The drawbacks of using large number of needles are: (1) longer procedure times, (2) longer patient recovery times, and (3) longer treatment times.

According to the invention, nested particle swarming strategies are used to solve the HDR inverse planning problem. First, kinetic particles with zero momentum are allowed to stabilize within the tumor (i.e., in a cross-section) or near the tumor to establish the initial locations. Then, an initial velocity or momentum is assigned to each kinetic particle, which pushes these particles to traverse the tumor along a desired direction. Finally, the path followed by each particle is mapped to an implant trajectory and each discrete position in this path as a potential position for a radioactive source. From these potential positions, the best ones are selected through our filtering process that uses least distance programming. Again, the prescribed dose is an input parameter provided by the physician.

The invention is used determine optimal and reliable implant trajectories using a minimal number of implants while meeting the prescription. It also allows flexible configuration in order to obtain plans with different levels of dose homogeneity. In short, the invention minimizes the number of implants and optimizes implant trajectories. The current commercial system can only calculate dwell times once the implants are in place. Thus, the invention may significantly improve HDR systems by providing the following key aspects: (1) optimal implant trajectories with minimum number of implants; (2) real-time imaging to guide physicians for implant placement; and, (3) real-time assessment for manual errors while guiding radiation including implant placement (i.e., positioning needles).

The invention and its attributes and advantages will be further understood and appreciated with reference to the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which:

FIG. 1 illustrates the pseudo-code according to one embodiment of the algorithm according to the invention.

DETAILED DESCRIPTION

Figure 2:
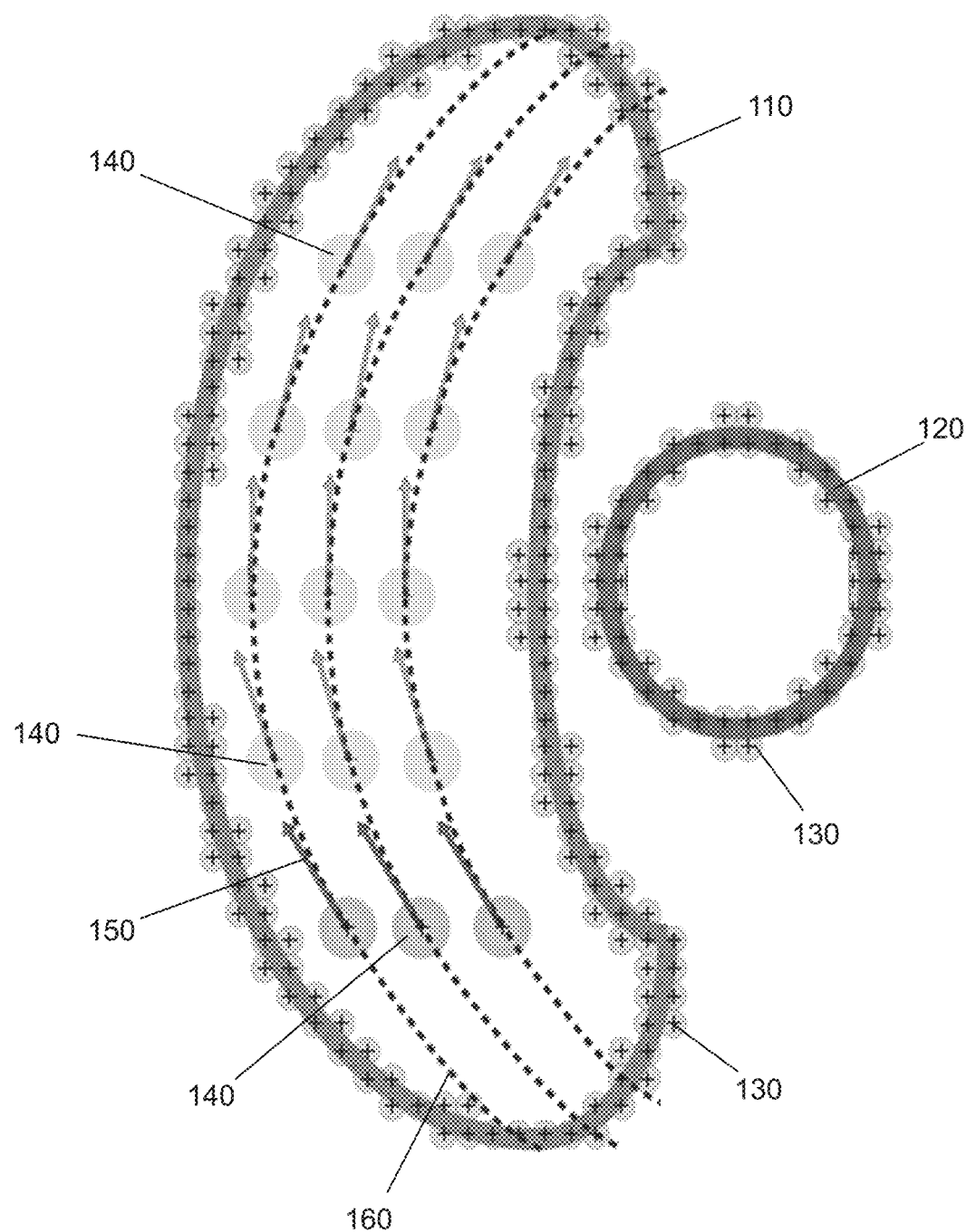
FIG. 2 is a schematic diagram illustrating the algorithm according to the invention.

The invention is based on the idea that physical models can be used to guide an optimization algorithm consisting of the interactions of a system of stationary and moving particles, such that a desired behavior can be simulated in order to obtain an optimum maximum or minimum state. Specifically, the invention is inspired by particle swarm optimization that evolves in time until mapping its state of minimum energy to optimal locations of radiation sources in radiotherapy and radiosurgery. In particular, the invention deviates from the classical PSO algorithm where a particle represents a potential solution of the optimization function by using the whole swarm or particle distribution as the solution.

Tumors, critical organs and other tissues are modeled as geometric volumes, whose surfaces have an associated potential function. The radiation source is modeled as kinetic particles subject to the forces from the potential functions from both the particles and the various geometric objects. The final configuration of the swarm of particles including their trajectories is the treatment plan. The term "swarm" is also referred to as "map". Each particle includes a particular location or position such that the particles in their entirety create the swarm or map.

The geometric characteristics of the treatment case are propagated throughout all the system so that a particle in the interior of the tumor can be aware of near-by critical organs or other tissues.

The steps typically involved with radiation therapy treatment planning patient imaging, target definition/structure contouring, dose prescription, beam configuration optimization, plan generation, quality assurance assist in formally defining the characteristics of the algorithm according to the invention.

Patient representation uses patient geometrical information described using set notation where V represents the set of all voxels in a CT or MRI scan of the patient, T represents the set of tumor voxels, $C_i$ represents the set of voxels for the $i^{th}$ critical structure. It can be noted that T and $C_i$ are pairwise disjoint. Finally, $\partial T$ and $\partial C_i$ denote the voxels on the surface of the tumor and critical structures.

The ideal dose distribution is a function that maps all voxels in V into a real interval prescribed by the physician, which corresponds to the minimum and maximum dose per voxel. The objective dose distribution is presented as:

$$D^*: V \rightarrow [a,b] \in \mathbb{R} \quad \text{(Equation 1.0)}$$

For critical structures, the minimum dose is 0, while the maximum dose is determined by organ/tissue specific radiation tolerance. For the tumor, the minimum dose is determined by tumor control probability, and the gap between minimum and maximum dose, i.e., b−a indicates the required dose uniformity.

Dose calculation includes a particle, $p_i$ defined as an entity that has a location: $\vec{x}_i = [x_i, y_i, z_i]$, a velocity: $\vec{v}_i = [v_{x_i}, v_{y_i}, v_{z_i}]$, a type: static or kinetic, and a potential function (otherwise referred to as a potential field).

Optimization is performed in two phases: PSO and deterministic optimization. For PSO, particles are divided in two disjoint sets according to their type K or S, for kinetic and static particles, respectively. The particle potential functions are created from the corresponding radiation source dose distribution and the prescribed dose distributions. For static particles, the static potential field, $U_s$ is pre-computed. For a kinetic particle $p_i$, the total external force incident on it is computed by the negative gradient of the total potential field of all particles:

$$\Sigma_{j \neq i} \vec{F}_j = -\vec{\nabla} \Sigma_{j=i} U_j = m \cdot \vec{a}_i \quad \text{(Equation 1.2)}$$

where m stands for the mass of particle $p_i$. The total external potential incident on a particle can also be expressed by:

$$-\vec{\nabla} U_i = -\vec{\nabla} (U_{K-\{p_i\}} + U_s) \quad \text{(Equation 1.3)}$$

Each particle's acceleration, $\vec{a}_i$, is calculated in order to update the velocity and position of each particle in a given time step $\Delta t$, respectively:

$$\vec{v}_i(t) = \vec{v}_i(t-1) + \vec{a}_i(t-1) \cdot \Delta t \quad \text{(Equation 1.4)}$$

$$\vec{x}_i(t) = \vec{x}_i(t-1) + \frac{\vec{v}_i(t) + \vec{v}_i(t-1)}{2} \cdot \Delta t \quad \text{(Equation 1.5)}$$

This process is repeated until a maximum time, $T_{max}$, is reached or a tolerance error, $\xi$, is achieved. Once a steady location of particles is achieved, particle positions are translated to radiation sources' positions in the treatment plan. In the deterministic optimization phase, numerical techniques such as non-negative least squares, least distance programming, linear programming, etc., are used to further refine the plan produced by PSO. The pseudo-code according to one embodiment of the algorithm is shown in FIG. 1.

Given an initial kinetic particle swarm and a precomputed potential, each particle position gets updated according to the total external forces. This process is repeated until a stable configuration of particles is reached or a minimum error is achieved. The algorithm returns the final stable swarm, or final map of particle locations.

Depending on the application, kinetic particles are initialized with an initial momentum. For the initial PSO phase, all kinetic particles are looped over one at a time. The current particle is excluded from the current total potential field (U). The negative gradient of the potential field (∇U) is computed and the position of the current particle is updated using the motion equations 1.2, 1.4, and 1.5 above. After updating all particles, the total distance variation of the whole particle distribution is determined; if it is less than a given threshold, the process stops, otherwise the process repeats. In an alternative embodiment, the process stops when a number of iterations reaches a certain threshold value. In order to compute a final dose distribution, dwell times are determined and negligible dwell times are filtered out. A dwell time is the length of time for delivering a radiation dose. A dose-volume histogram can be generated from the final dose distribution. A dose-volume histogram facilitates understanding the quality of a treatment plan in terms of its dose distributions. Specifically, it provides the amount of volume per biological structure that received at least a certain percentage of the maximum dose.

FIG. 2 is a schematic diagram illustrating the algorithm 100 according to the invention. A tumor mass 110, along with other critical structures 120 such as critical organs, and normal tissues are defined and modeled such as geometric volumes. The tumor mass 110 and other critical structures 120 are covered with static particles 130, each having its own potential function. It is contemplated that each potential function may be the same or different. More specifically, each potential function of each static particle 130 provide the potential field for the surface of the tumor volume and organ or tissue volumes.

A radiation source is modeled as kinetic particles 140, or spherical high dose volumes, which are positioned within a cross-section of the tumor mass 110 or outside the tumor mass 110, but nearby. The kinetic particles 140 each have its own potential function. It is contemplated that each potential function may be the same or different. The kinetic particles 140 are subject to the forces from the potential functions from both the kinetic particles 140 and the various geometric objects. The kinetic particles 140 search for a minimum potential and stabilize.

As shown in FIG. 2, the kinetic particles 140 are displaced toward the left side due to the placement of other critical structures 120 on the right side of the tumor mass 110. This effect is due to the potential field associated with the other critical structures 120. Specifically, the kinetic particles 140 move under the influence of a potential field. When the kinetic particles 140 are given an initial velocity (otherwise referred to as momentum) as shown by the arrow 150, the kinetic particles 140 traverse the tumor mass 110 in evenly spread trajectories 160. The final configuration of the swarm of particles, or spherical high dose volumes, including their trajectories 160 is the treatment plan.

Figure 3:
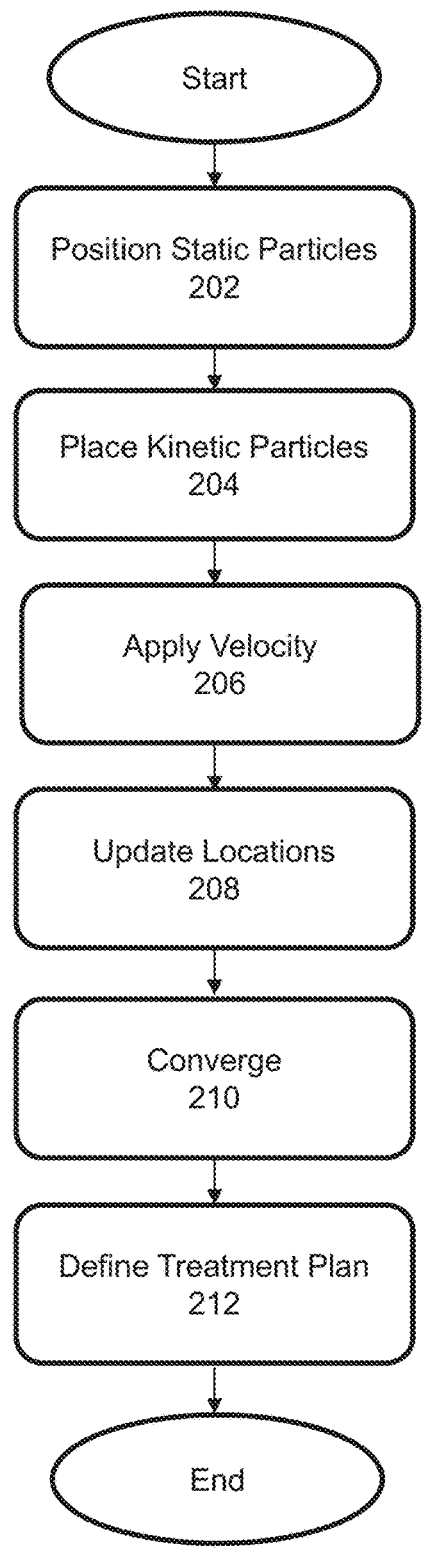
FIG. 3 is a flow chart of an exemplary optimization method for radiation therapy planning according to the invention.

FIG. 3 illustrates a flow chart of the steps of an optimization method 200 for radiation therapy planning according to one embodiment of the invention. Structures are defined as one or more tumor masses 110 and surrounding critical structure 120 or normal structures. Static particles 130 are positioned on the surfaces of the critical structures 120 at step 202. The static particles 130 are positively "charged" creating a static potential field (as defined by a function). It is contemplated that the static potential field is constrained to a prescribed dose distribution. The static particles 130 may be applied randomly or according to a specified pattern.

At step 204, one or more kinetic particles 140 or spherical high dose volumes are positioned near the tumor mass 110 or within the interior volume of the tumor mass 110, i.e., a cross-section of the tumor mass 110. The kinetic particles 140 are in an initial position such that all kinetic particles 140 define a map of locations, or swarm. An arbitrary potential field is applied to the kinetic particles 140 creating a dynamic potential field (as defined by a function). It is contemplated that the dynamic potential field is constrained to a dose distribution of a radiation source.

At step 206, an initial velocity/momentum 150 is applied to each kinetic particle 140 of the swarm. The initial velocity/momentum 150 may be applied such that it is parallel to a principal implant direction of a radiation source. A force value incident upon the kinetic particles 140 is calculated from the potential fields. For example, the force may be a negative gradient of both the dynamic potential field and the static potential field. The force value incident upon each spherical high dose volume is used to arrive at an acceleration value.

At step 208, the first location of each kinetic particle 140 is updated such that all kinetic particles 140 define a new map of locations. The kinetic particles 140 continue to move until the maps converge to a variation of distance that is less than a given threshold value at step 210. Alternately, the kinetic particles 140 move until a number of iterations reaches a certain threshold value.

At step 212, the treatment plan is defined. The location of each kinetic particle 140 may be recorded or simply translated to define the radiosurgery plan. A radiation source executes the treatment plan. Specifically, location of each kinetic particle 140 translates to a radiation dose that is generated by a radiation source. Depending on the modality used, the point for receiving a radiation dose may be a beam location or interstitial implant trajectories 160.

The optimization method 200 for radiation therapy planning according FIG. 3 may further comprise determining a length of time the radiation dose is to be delivered (i.e., dwell time) such that the dose distribution is within a prescribed ideal dose or at least as close to a prescribed ideal dose as possible. The length of time the radiation dose is to be transmitted may be determined using one or more algorithms selected from the following: least squares, non-negative least squares, least distance programming, linear programming, etc. The optimization method 200 according to the invention may also be used to create a dose-volume histogram from a dose distribution.

According to one particular embodiment, the invention is applied to Gamma Knife® radiosurgery. Dose kernels are mapped to a potential function associated to each kinetic particle 140 in the swarm and the interaction among them converges to a stable configuration. The locations of the kinetic particles 140 are then translated to dwell locations and the non-negative least squares algorithm is used to calculate the dwell time of each kernel aiming to meet the dose prescription.

Each kinetic particle 140 is assigned a potential function $$\frac{1}{\alpha \cdot r},$$

where r is the distance from the kinetic particle 140 to a voxel, and a is a constant scaling factor directly proportional to the dose kernel radio to be used in the simulation. The intuition behind such an arrangement is that the kinetic particles 140, i.e. the spherical high dose volumes, should not be too dose to each other, and should not be too close to the boundary or the critical structures 120.

The kinetic particles 140 are initialized at random positions with zero initial velocities or zero momentum 150. The quantity and potential functions associated to each kinetic particle 140 are calculated from an approximate solution obtained from the following constrained integer-linear problem:

$$\underset{y_i \in Z^+}{\text{minimize}} |a \cdot y - b|$$

subject to $\|y\|_1 \leq n$ where a is a row vector containing the volume each kernel can cover with a high density dose, y is a column vector representing the distinct kernel spot sizes to be used, b is the cardinality of T, and n is the cardinality of K. The potentials $U_s$ and $U_K$ created by static and kinetic particles 140 respectively are computed. In each iteration, the locations of the kinetic particles 140 are updated based on the forces from the potential field until they converge. The PSO phase outputs the locations of each spherical high dose volume. To complete a particular radiosurgery plan, the dwell or beam-on times may be needed for each location. With $\dot{D}_j$ and $t_j$ be the dose rate and beam-on times for each particle/spherical high dose volume, and D* be the optimal desired dose distribution. Non-negative least squares is used to calculate the optimal beam-on times:

$$\text{minimize } \|\Sigma_j \dot{D}_j t_j - D^*\|_2^2 \text{ subject to } t_j \geq 0$$

The optimization algorithm as applied to a C-shaped tumor 3D geometric object surrounding a spherical critical structure includes a prescription targeting 100 arbitrary dose units to the tumor while delivering 0 arbitrary dose units to the critical organ, which achieved convergence within 20 to 40 iterations.

Homogeneous kernel spot sizes were used. Kinetic particles start at random locations inside the tumor and at each iteration they evolve, spreading evenly throughout the volume through the dynamic interactions among them and the potential field from the structure's surfaces. Particles get pushed in the opposite direction from the critical organ, which reflects the geometrical awareness imposed onto them by the potential field associated with the critical organ. Non-negative least squares is used to filter out those locations that are either redundant or that do not contribute to meeting the prescription. The particles distribute evenly along the tumor's volume while avoiding regions close to the critical organ.

Figure 4:
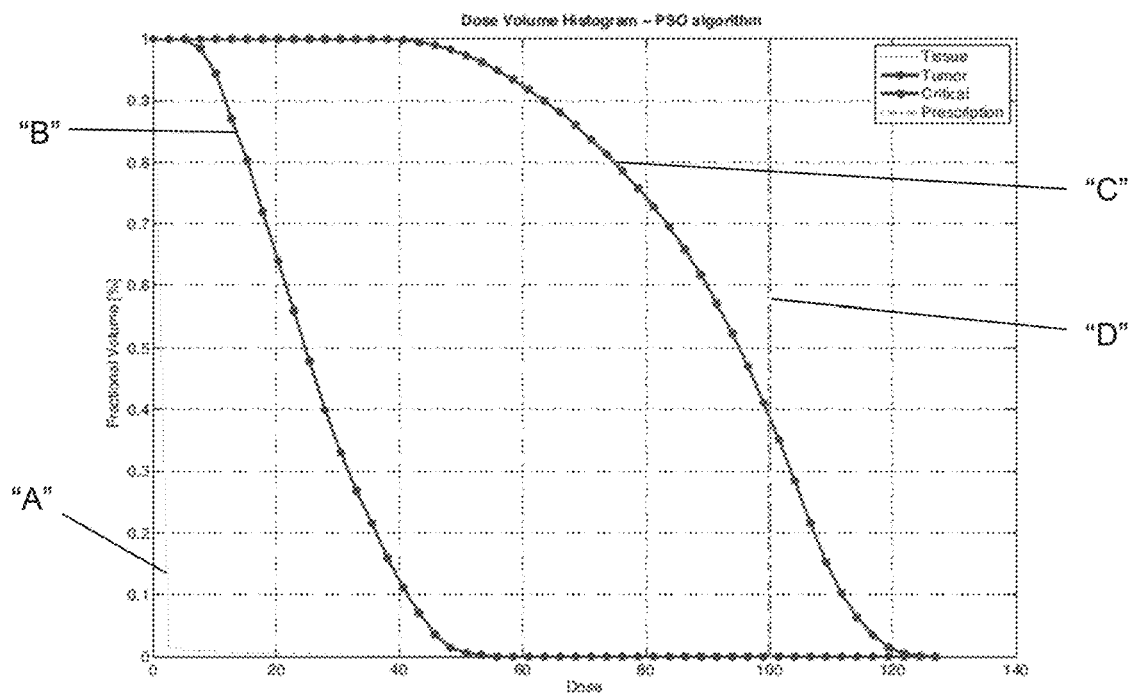
FIG. 4 illustrates a dose-volume histogram according to one embodiment of the invention.
Figure 5:
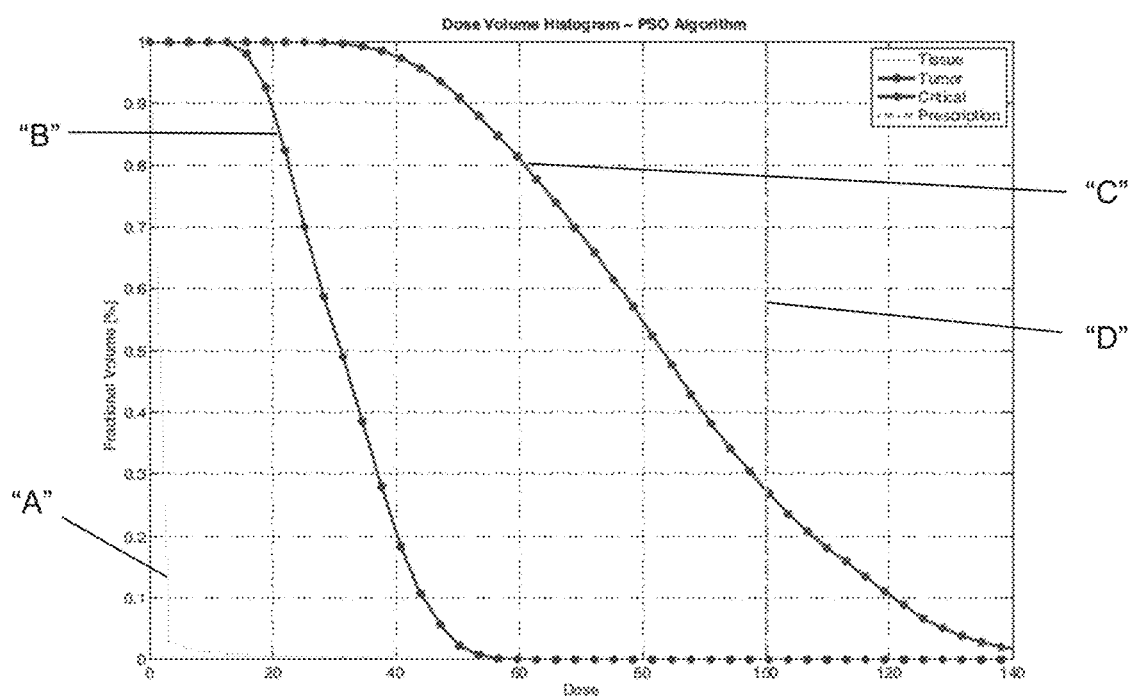
FIG. 5 illustrates a dose-volume histogram according to another embodiment of the invention.

FIG. 4 and FIG. 5 illustrate dose-volume histograms. Specifically, FIG. 4 illustrates a dose-volume histogram of homogeneous kernel spot sizes using 4 mm dose kernels. FIG. 5 illustrates a dose-volume histogram of heterogeneous kernel spot sizes using 4 mm and 8 mm dose kernels. In the histograms, the horizontal axis is the dose, while the vertical axis is the percent volume. There is a line for each structure of interest, which describes the amount of dose delivered to a given percent volume. Specifically, line "A" is tissue structure, line "B" is tumor structure, line "C" is critical structure (i.e., organ), and line "D" corresponds to the prescription. The quality of the plan is comparable to the manually obtained clinical plans, which aims to cover the target tumor volume with 50% of the maximum dose.

According to another particular embodiment, the invention is applied to high-dose rate (HDR) brachytherapy. As mentioned previously, HDR brachytherapy is performed as a four-step process: catheter or implant placement, image contouring, dwell time optimization, and dose delivery.

Each kinetic particle is mapped to a radiation source and a set of initial conditions is imposed, which include defining starting positions and initial velocities in the direction of previous clinical implants. The key idea of this embodiment is to let the particles in the swarm to traverse the tumor and record its particles' trajectories. The trajectory of each particle is mapped as the implant trajectory, and the final dose delivered is calculated using each particle position as the center of a radiation source, further optimized using least-distance programming.

Each needle is modeled as the trajectory of a kinetic particle with a potential function $$\frac{1}{r^2},$$

where r is the distance from the particle. Static particles are randomly placed on the surface of the prostate and various critical structures such as the rectum, urethra, and bladder. The potential function of each static particle is $$\frac{1}{r^2}.$$

The key to this embodiment is the initial velocity of the kinetic particles. Clinically, the bevel needles used have a curvature constraint and can bend up to a certain degree value. The initial velocity of the kinetic particles ensures that the curvature constraint will not be violated during the simulation. The total number of kinetic particles—the number of needles—is specified by the user.

To determine the initial position of the kinetic particles, the kinetic particles are randomly placed within a cross-section of the tumor with zero velocity and constrained to move within that cross-section. Once the particles stabilize, they are given a velocity vector parallel to the principal needle direction typically used in a clinical setting. After the trajectories converge, a third-degree polynomial regression is applied to smooth the final particles' trajectories, which are the final needle positions. To calculate the dwell time, the following formulation of a least-distance programming (LDP) problem is used:

Minimize $\|x\|_2^2 + \|\Lambda_{max}s\|_2^2 + \|\Lambda_{min}t\|_2^2$ subject to $Dx - s \leq b_{max}$ $Dx + t \geq b_{min}$ The vectors $b_{min}$ and $b_{max}$ specify the minimum and maximum dose for each voxel. The matrix D is the dose matrix of each discretized position along the needles. Ideally, all prescription constraints are met and $Dx \geq b_{min}$ and $Dx \leq b_{max}$, while minimizing the total treatment time $\|x\|$. However, this is never feasible. To overcome this, slack variables s and t are added to the constraints to ensure feasibility. The weighting variables $\Lambda_{max}$ and $\Lambda_{min}$ (both are diagonal square matrices) reflect the "importance" of the various constraints. The goal of the objective function is to minimize the total treatment time while making sure that as few as possible voxels are violating the prescription constraints.

Given a specified number of implants, the algorithm according to the invention finds the optimal trajectories that meet clinical goals. In addition, the algorithm reduces the number of implants. It is contemplated that implant procedures may be performed under the guidance of such pre-calculated trajectories. If the pre-calculated implant trajectories are not followed perfectly, the impact is negligible. Furthermore, it is shown that the algorithm obtains homogeneous dose plans.

Figure 6:
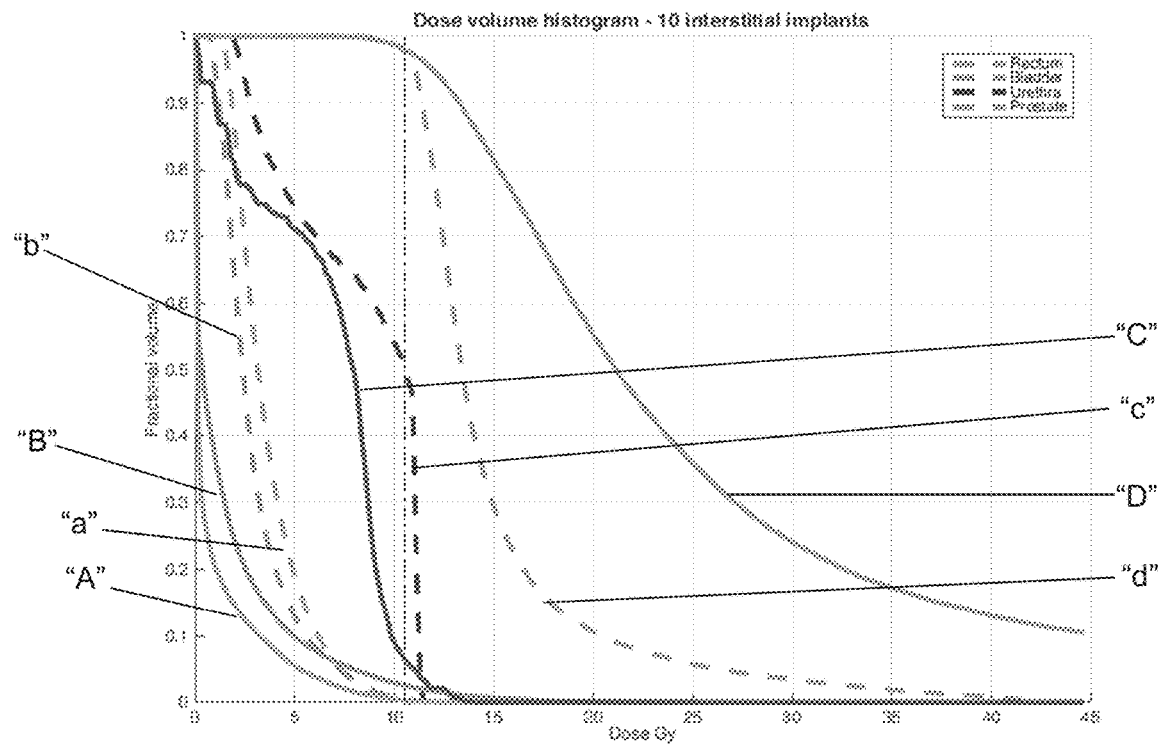
FIG. 6 illustrates a dose-volume histogram according to one embodiment of the invention.

FIG. 6 shows the dose-volume histogram comparisons between the plan achieved by the algorithm of the invention (denoted by capital letters "A", "B", "C", "D") and the previously used clinical plan (denoted by lowercase letters "a", "b", "c", "d"). Each letter combination shown in FIG. 6 illustrates a particular organ: "A", "a" represents the rectum, "B", "b" represents the bladder, "C", "c" represents the urethra, "D", "d" represents the prostate.

With the dose-volume histogram illustrating the amount of dose delivered to a given percent volume, line "D" for the prostate in denotes that 98% of the prostate receives at least the prescribed dose. As shown in FIG. 6, all the prescription goals are achieved and is comparable to the previously used clinical plan. Although the algorithm of the invention produces less uniform results as shown by lines "A", "B", "C", "D" than the clinical plan shown by lines "a", "b", "c", "d" this may represent a superior result in that these dose inhomogeneities are mainly localized inside the target, which may allow higher cell damage and tumor control, while meeting the radiation tolerance constraints for all critical structures.

The algorithm proves to produce high quality plans for a variety of setups varying in the number of needles used. A higher implant density is able to lower dose impact to the urethra, rectum and bladder. Finally, while the clinical plan for this case used 17 needles, the invention shows to be able to produce high quality plans using 10 needles corresponding to a 41% reduction.

It is expected that implant placement procedures may be performed under the guidance of pre-calculated trajectories. In order to assess the applicability of our generated plans, we randomly perturb the trajectories to mimic the manual implant errors. However, least distance programming is able to compensate for these errors in perturbations.

Figure 7:
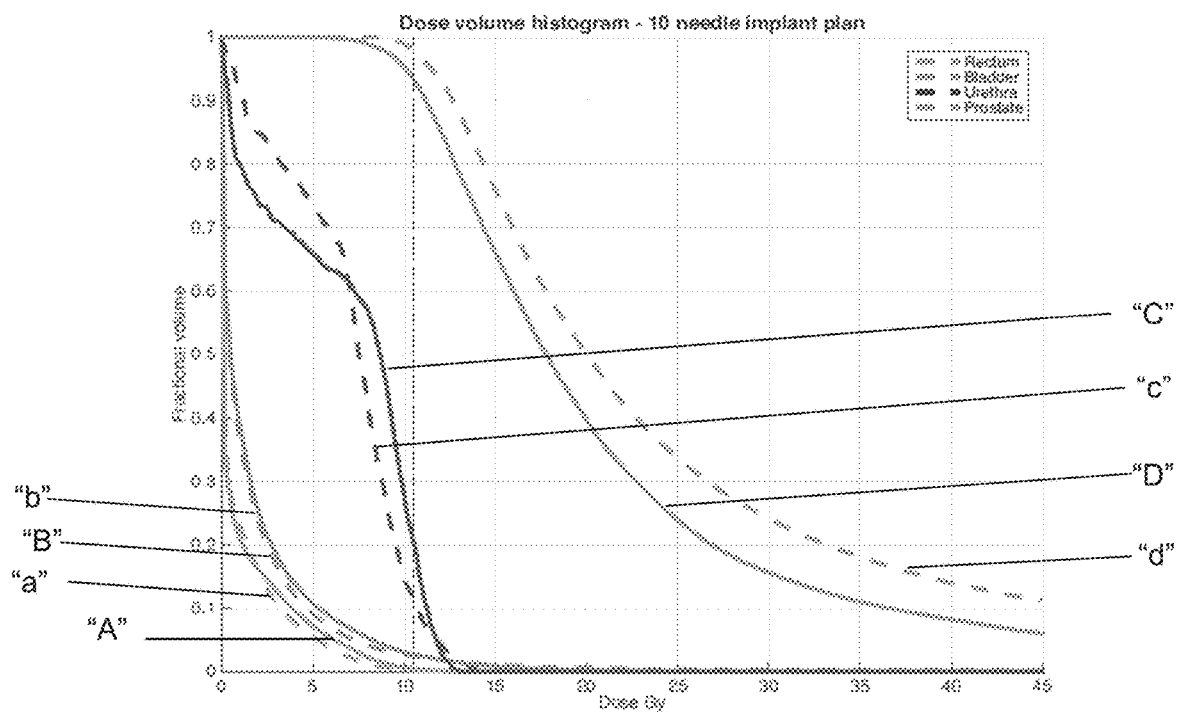
FIG. 7 illustrates a dose-volume histogram according to another embodiment of the invention.

Even with the understanding that HDR brachytherapy plans inherently have inhomogeneous dose distributions, due to the nature of the radiation sources that deliver a very high dose to those tissues close to the implants, the versatility of the optimization technique according to the invention is tested by trying to obtain uniform dose distributions. This is done by varying the weighting variables $\Lambda_{max}$ and $\Lambda_{min}$ to reflect the importance of lower doses deposited inside the target. Higher dose homogeneity can be obtained, but with a slight change in the objective function of the least distance programming optimization, i.e.:

Minimize $\lambda(\|x\|_2^2) + (1-\lambda)(\|\Lambda_{max}s\|_2^2 + \|\Lambda_{min}t\|_2^2)$ subject to $Dx - s \leq b_{max}$ $Dx + t \geq b_{min}$ where $0 \leq \lambda \leq 1$ FIG. 7 displays the results. Similar to FIG. 6, each letter combination shown in FIG. 7 illustrates a particular organ: "A", "a" represents the rectum, "B", "b" represents the bladder, "C", "c" represents the urethra, "D", "d" represents the prostate. As shown in FIG. 7, the capital letters "A", "B", "C", "D" denote the plan achieved by the modified objective function and lowercase letters "a", "b", "c", "d" denote the previously used algorithm (capital letters "A", "B", "C", "D" of FIG. 6).

As shown, higher implant density improves homogeneity, but since the algorithm according to the invention is able to generate implant trajectories that bend intelligently along the prostate boundary, the critical organs rectum and bladder always remain underdosed (with respect to the clinical plan), while the urethra suffers a slight overdosage due to a better implant utilization inside the prostate.

As described above, the invention was applied to Gamma Knife® radiosurgery and High-Dose Rate Brachytherapy; however, any radiation therapy modality is contemplated including for example a particle therapy machine or a lower dose rate Brachytherapy seed.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A method for providing a radiotherapy or radiosurgery treatment plan, comprising:
    using a particle swarm as a solution to an optimization problem, wherein the solution is a location of the particle swarm in a minimum energy state; and
    providing the location for a radiation dose from a radiation source.

2. The method of claim 1, wherein the optimization problem is:

$$\underset{t}{\text{minimize}} \left\| \sum \dot{D}_j t_j - D^* \right\| \text{ subject to } t_j \geq 0,$$

where $D^*$ is an ideal dose distribution or a prescribed dose, $\dot{D}_j$ is a dose rate contributed by a j-th candidate beam, and $t_j$ is a beam-on time for the j-th candidate beam, a constraint $t_j \geq 0$ is a non-negative beam-on time.

3. The method of claim 2, further comprising the step of:
    solving the optimization problem when two or more beam-on times $t_j$ are found so that a created dose distribution $\Sigma_j \dot{D}_j \times t_j$ is as close to the ideal dose distribution or the prescribed dose $D^*$ as possible.

4. The method of claim 1, further comprising the step of:
    determining a length of time the radiation dose is transmitted to the location using one or more algorithms selected from the group consisting of: least squares, non-negative least squares, least distance programming, and linear programming.

5. The method of claim 1, wherein the using step further comprises the steps of:
    modeling a tumor as a geometric volume comprising geometric objects with potential functions;
    modeling the radiation source as a set of particles subject to forces from the potential functions from the geometric objects;
    achieving a steady location of the set of particles;
    translating a position and a trajectory of each particle of the set of particles to a location of the radiation source; and
    providing a treatment plan comprising the location of the radiation source.

6. The method of claim 5, further comprising the step of:
    determining a length of time the radiation dose is transmitted to the location using one or more algorithms selected from the group consisting of: least squares, non-negative least squares, least distance programming, and linear programming.

7. The method of claim 5, wherein each particle $p_i$ of the set of particles includes a location: $\vec{x}_i$ for each particle $p_i = [x_i, y_i, z_i]$, a velocity: $\vec{v}_i$ for each particle $p_i = [v_{x_i}, v_{y_i}, v_{z_i}]$, a type: static or kinetic, and a potential function.

8. The method of to claim 7, further comprising the step of:
    pre-computing a static potential field $U_s$ for each particle $p_i$ of the set of particles that is of the static type.

9. The method of claim 7, wherein a total external potential incident on each particle $p_i$ of the set of particles is:

$$-\vec{\nabla} U_i = -\vec{\nabla}(U_{K-\{p_i\}} + U_S)$$

wherein $U_S$ is a static potential field of the particle $p_i$ of the set of particles that is of the static type and $U_K$ is a kinetic potential field of the particle $p_i$ of the set of particles that is of the kinetic type.

10. The method of claim 7, further comprising the step of:
    calculating an acceleration $\vec{a}_i$ of each particle $p_i$ of the set of particles to update the velocity and the location of each particle $p_i$ of the set of particles in each time step $\Delta t$, repsectively:

$$\vec{v}_i(t) = \vec{v}_i(t-1) + \vec{a}_i(t-1) \cdot \Delta t$$

$$\vec{x}_i(t) = \vec{x}_i(t-1) + \frac{\vec{v}_i(t) + \vec{v}_i(t-1)}{2} \cdot \Delta t.$$

11. A method for Gamma Knife radiosurgery, comprising the steps of:
    assigning a potential function $$\frac{1}{\alpha \cdot r}$$

to each particle, wherein r is a distance from a particle to a voxel, and a is a constant scaling factor directly proportional to a dose kernel:
    initializing kinetic particles K at random positions with zero initial velocities or zero momentum;
    calculating potential functions associated to each particle using an approximate solution obtained from a constrained integer-linear problem:

$$\underset{y_i \in Z^+}{\text{minimize}} |a \cdot y - b|$$

$$\text{subject to } \|y\|_1 \leq n$$

wherein a is a row vector containing a tumor volume, each kernel can cover with a high-density dose, y is a column vector representing kernel spot sizes, b is a cardinality of a set of tumor voxels T, and n is a cardinality of the kinetic particles K;
    computing a potential field $U_s$ of static particles and a potential field $U_K$ of kinetic particles K;
    updating in each iteration, a location of each kinetic particle of the kinetic particles K based on forces from the potential field $U_K$ of kinetic particles K until the location of each kinetic particle converge;
    outputting a location of a spherical high dose volume for each kinetic particle.

12. The method of claim 11, further comprising the step of:
    calculating optimal dwell times using a non-negative least squares problem:

$$\text{minimize } \|\Sigma_j \dot{D}_j t_j - D^*\|_2^2 \text{ subject to } t_j \geq 0$$

where $\dot{D}_j$ is a dose rate contributed by a j-th candidate beam, $t_j$ is a dwell time for the j-th candidate beam of each spherical high dose volume, and D* is an optimal desired dose distribution.

13. The method of claim 11, wherein the kernel spot sizes are homogeneous.

14. The method of claim 13, further comprising the step of:
creating a dose-volume histogram of homogeneous kernel spot sizes.

15. A method for high-dose rate (HDR) brachytherapy, comprising the steps of:
providing a tumor modeled as a geometric volume;
mapping each kinetic particle to a radiation source;
imposing a set of initial conditions on each kinetic particle, the set of initial conditions comprising defined starting positions and initial velocities in a direction of each needle of a plurality of needles;
recording a trajectory of each kinetic particle; and
calculating a final dose delivered using a position of each kinetic particle as a center of the radiation source.

16. The method of claim 15, further comprising the steps of:
modeling each needle as the trajectory of each kinetic particle with a potential function $$\frac{1}{r^2},$$

where r is a distance from a kinetic particle, and
placing randomly static particles on a surface of the geometric volume of the tumor with a potential function $$\frac{1}{r^2},$$

where r is a distance from a static particle.

17. The method of claim 15, wherein the tumor is located on a prostate organ.

18. The method of claim 15, further comprising the step of:
calculating a dwell time using a least-distance programming (LDP) problem:

$$\text{Minimize } \|x\|_2^2 + \|\Lambda_{max}s\|_2^2 + \|\Lambda_{min}t\|_2^2$$

$$\text{subject to } Dx - s \leq b_{max}$$

$$Dx + t \geq b_{min}$$

wherein vector $b_{min}$ is a minimum dose for each voxel and vector $b_{max}$ is a maximum dose for each voxel, matrix D is a dose matrix of each discretized position along the plurality of needles, s and t are variable constraints to ensure feasibility, $\Lambda_{max}$ and $\Lambda_{min}$ are weighting variables.

19. The method of claim 15, further comprising the step of:
determining a length of time the final dose is transmitted to a location using one or more algorithms selected from the group consisting of: least squares, non-negative least squares, least distance programming, and linear programming.

20. The method of claim 15, wherein the radiation source is an Ir-192 source.

* * * * *